US00PP23443P2

(12) United States Plant Patent
Okie

(10) Patent No.: US PP23,443 P2
(45) Date of Patent: Mar. 5, 2013

(54) PEACH TREE NAMED 'CANDY CANE'

(50) Latin Name: ***Prunus persica* (L.) Batsch**
Varietal Denomination: Candy Cane

(75) Inventor: William Okie, Warner Robins, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/136,364

(22) Filed: Jul. 29, 2011

(51) Int. Cl.
*A01H 5/00* (2006.01)

(52) U.S. Cl. ..... Plt./195

(58) Field of Classification Search ..... Plt./194, Plt./195, 196, 197, 198, 199
See application file for complete search history.

(56) References Cited

U.S. PATENT DOCUMENTS

| | | | |
|---|---|---|---|
| PP11,493 | P | 8/2000 | Werner et al. |
| PP11,564 | P | 10/2000 | Werner et al. |
| PP11,576 | P | 10/2000 | Werner et al. |
| PP11,902 | P2 | 6/2001 | Werner et al. |

*Primary Examiner* — Howard Locker

(74) *Attorney, Agent, or Firm* — Gail E. Poulos; John D. Fado; Lesley Shaw

(57) ABSTRACT

Description and specifications of a new and distinct ornamental peach tree with attractive peppermint-type flowers that is well-adapted to the Southeastern United States climate. 'Candy Cane' has flowers with various combinations of white, pink, and red color, a well as leaves that are variegated red and green.

5 Drawing Sheets

Figure 1:
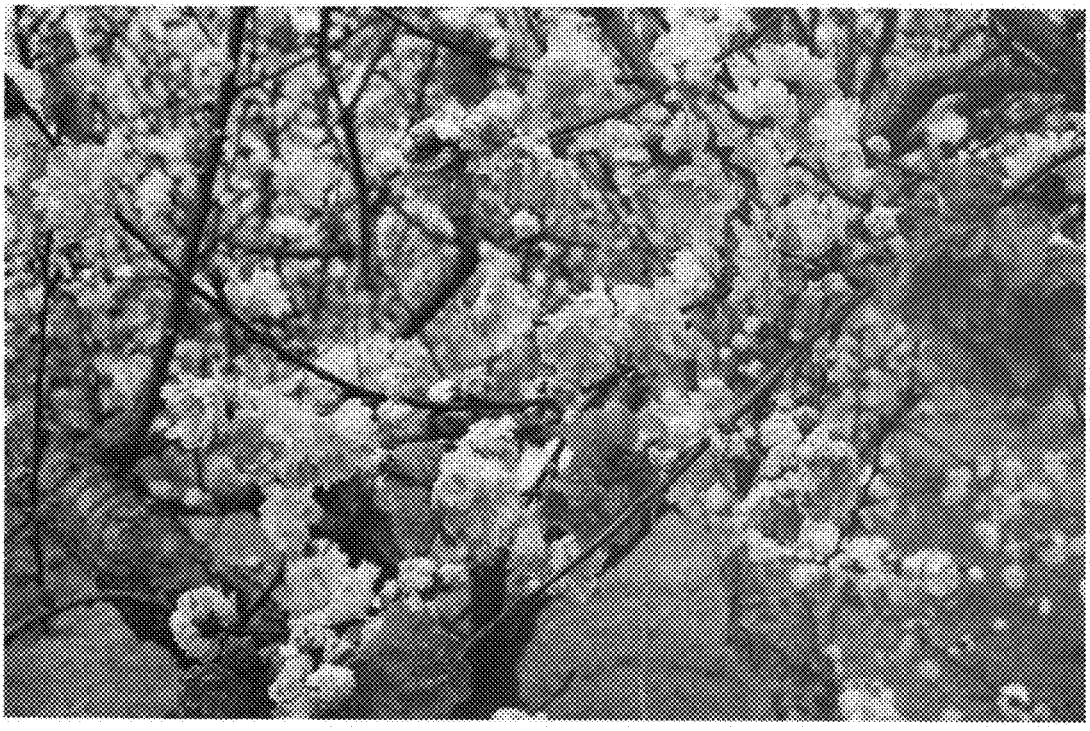

Latin name of the genus and species of the plant claimed: 'CANDY CANE' is a new ornamental peach tree that is a *Prunus persica* (L.) Batsch.

Variety denomination: The new ornamental peach tree claimed is of the variety denominated 'Candy Cane', *Prunus persica* (L.) Batsch.

BACKGROUND OF THE INVENTION

The present invention relates to the discovery of a new and distinct variety of ornamental peach tree, botanically known as *Prunus persica* (L.) Batsch, and herein referred to as 'CANDY CANE', as herein described and illustrated.

The new and distinct variety of ornamental peach tree 'CANDY CANE' originated as an open-pollinated selection of BY89P4594, which was an F2 selection from a hand pollinated cross of Shidaremomo seedling X Peppermint Stick made in 1985.

Plants and fruit of this new cultivar differ phenotypically from its parents. Seed of 'Shidaremomo' produced seedlings which were mostly red, single-flowered weepers but the tree used as a parent for 'CANDY CANE' was a red-leafed upright tree, suggesting it resulted from an outcross. Trees of 'Peppermint Stick' used as a pollen parent for 'CANDY CANE', had solid pink double flowers, apparently the result of using a bud from a pink-flowered reversion sector, but which genetically still carried the gene for variegated flowers. From the resulting hybrids BY86P238 was selected which had normal showy flowers and standard tree type. From a group of open-pollinated seedlings of BY86P238, BY89P4594 was selected with single, white and pink flowers, and green leaves with occasional red flecks. Open-pollinated seedlings of BY89P4594 were planted in Byron, Ga. in 1994. BY94P7706 was selected from these trees when it first bloomed in 1996, because of its tri-colored flowers and variegated foliage. The original tree was bud-grafted onto GUARDIAN™ rootstock and the resulting trees planted in Byron, Ga. in 1999. Third generation trees were bud-grafted onto GUARDIAN™ in 2007 and trees were planted at Byron, Ga. in 2008. There are no known effects of this standard rootstock on this scion variety. The present invention has been found to retain its distinctive characteristics through successive asexual propagations, as long as buds from shoots with tri-colored blooms are selected for propagation.

'CANDY CANE' has unique tree and fruit characteristics making it suitable for ornamental use. It is apparently homozygous for red leaf (GrGr), red flower (rr), double flower (dd), and unstable white flower ($w^v w^v$). The $w^v$ gene inconsistently inhibits anthocyanin (red color) production, so phenotypically, most leaves and stems appear green with various amounts of red streaks and sectors. As is typical of red-leaf peaches, the red color is most noticeable on new growth, and fades to a bronze-green on older leaves. Blossoms are very large, with buds reaching approximately 1.5 cm in diameter just before opening, and open blossoms reaching approximately 7 cm in diameter. Most flower parts are doubled or more. The showy petals display a combination of white, pink, and red colors, often within the same flower, similar to the variety 'Peppermint Stick'.

As the tree produces new growth, the unstable $w^v$ gene may become inactive and revert back to wild type (W) allowing red pigments to be expressed, or may become more stable showing no red color, similar to ww (white-flowered). This combination of three gene expressions in two tissue layers produces the striking variegation in flower, leaf, and stem color. If the reversion or stabilization occurs in the cells that produce a vegetative bud, the entire shoot arising from that bud may also change. Reversion to red (flower and leaf) or stabilization to no-red (green leaf and white flower) seems to be permanent for a given layer, although in sectors where the gene has stabilized no-red, rare red or pink flecks may still be seen.

To maintain the variegated form, nurserymen must propagate using buds from shoots with variegated red and green stems and leaves. Trees propagated from other types of shoots will not have the maximum variegation but are in themselves attractive ornamentals due to the very large flower size. For example, trees budded from red-leaved shoots will remain red-leaved and red-flowered.

The new variety has been named 'CANDY CANE'.

BRIEF DESCRIPTION OF THE PHOTOGRAPHS

Figure 2:
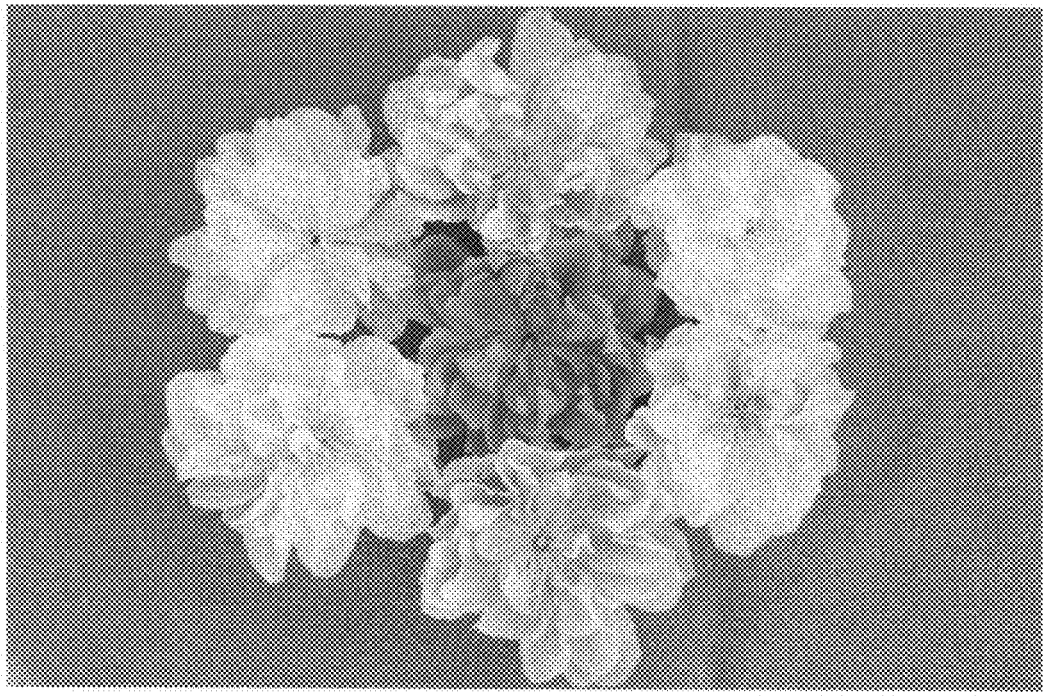
Figure 3:
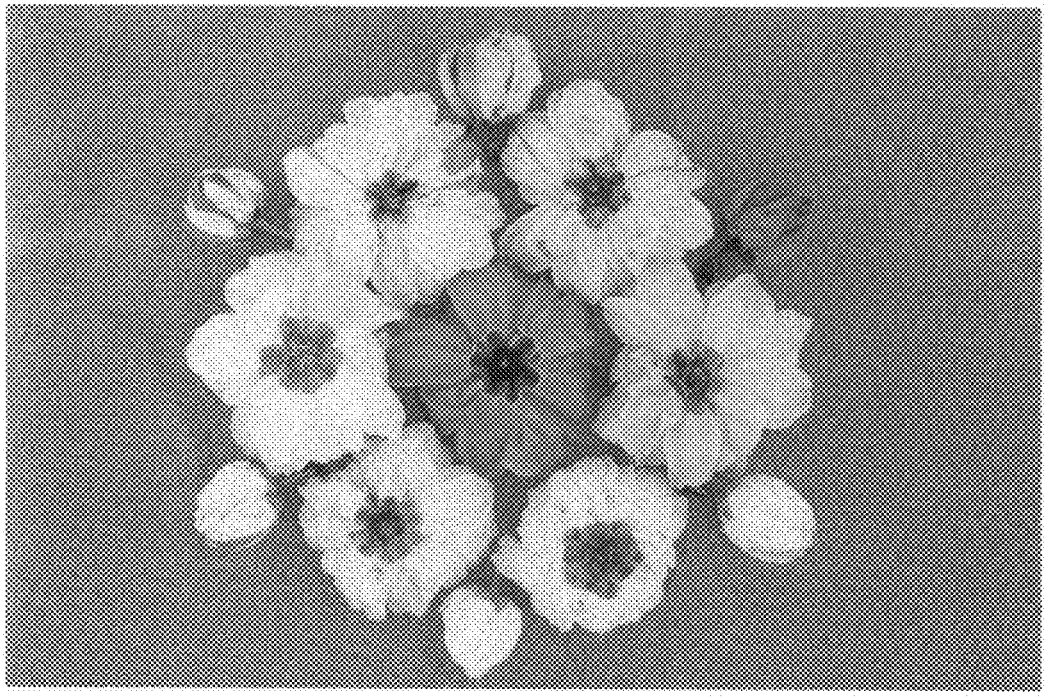
Figure 4:
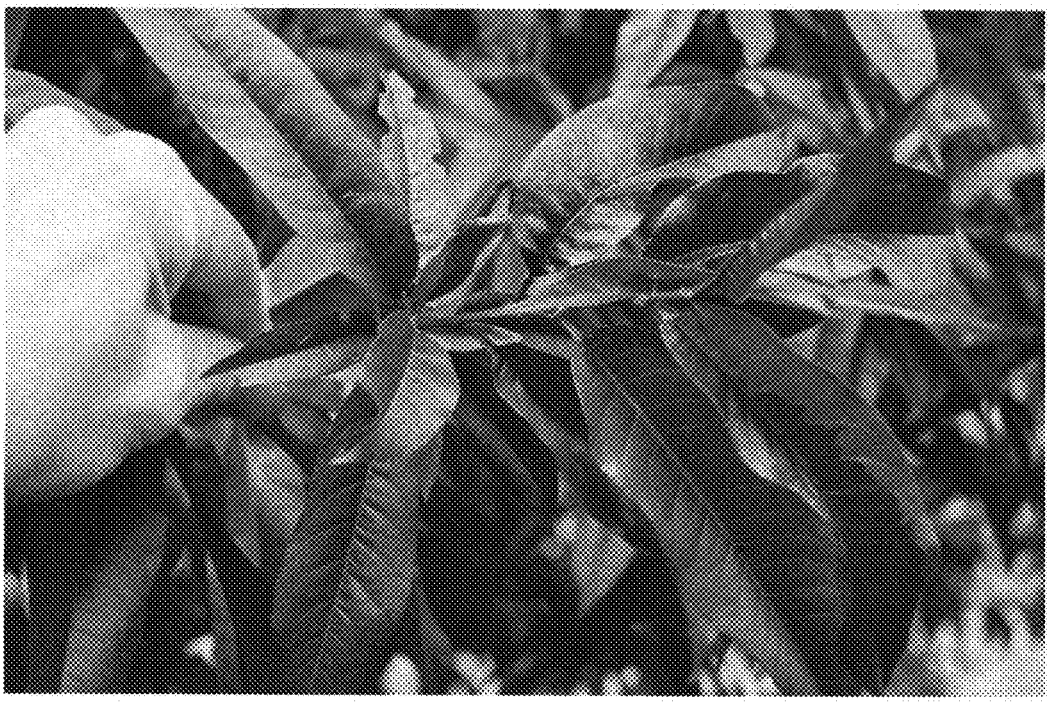
Figure 5:
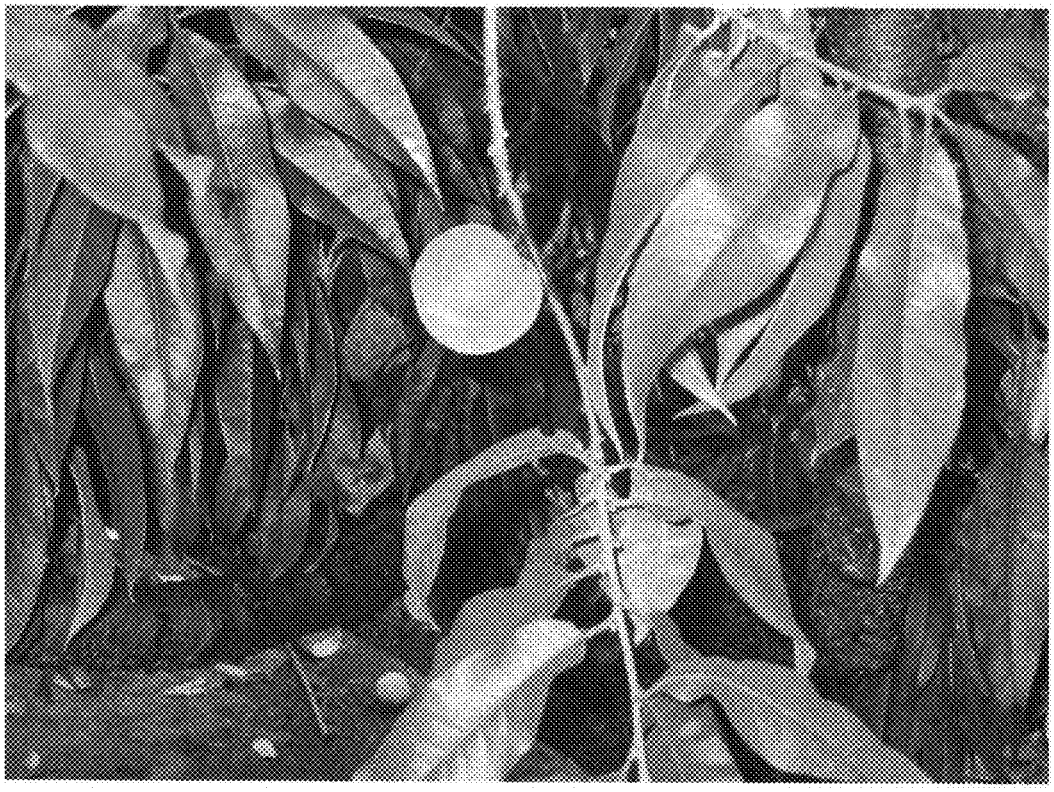

The accompanying photographs show typical specimens of the flower (FIGS. 1-3); leaf (FIG. 4), and mature fruit (FIG. 5) of the new variety in color as nearly true as it is reasonably possible to make in a color illustration of this character.

DETAILED DESCRIPTION OF THE NEW CULTIVAR

The following is a detailed description of the botanical and pomological characteristics of the subject ornamental peach. Color data are presented in Royal Horticultural Society (R.H.S.) Colour Chart (Third edition, 1995) designations.

Where dimensions, sizes, colors and other characteristics are given, it is to be understood that such characteristics are approximations of averages set forth as accurately as practicable.

The descriptions reported herein are from trees grown at Byron, Ga. in 2011 on GUARDIAN™ rootstock (third generation trees, 4 years old). The tree, flowers, and fruit of 'CANDY CANE' may vary in slight detail due to variations in soil type, cultural practices, and climatic condition. Color descriptions and other terminology are used in accordance with their ordinary dictionary descriptions, unless the context clearly indicates otherwise. Color designations are made with reference to The Royal Horticultural Society (R.H.S.) Colour Chart as indicated above. The plants used for these evaluations were planted in 2008.

Tree:

*Form*.—Semi-spreading and rounded if unpruned.

*Vigor*.—Moderately vigorous; tree growth of approximately 1 to 1.5 m in height and approximately 1 m in width occurs the first growing season in the field.

*Size*.—Trees are medium stature. Tree size after 4 years is approximately 4.5 m wide and approximately 4 m tall.

*Trunk*.—Trunk diameter at about 10 cm height is approximately 9 cm.

*Trunk texture*.—Medium smooth, but becoming rougher as tree ages.

*Trunk lenticels*.—Approximate number per square cm: 1-2. Size: large, approximately 10-12 mm length, horizontal on the trunk. Color: greyed orange (RHS 170C).

*Bark color*.—Older bark grayed-green (RHS 198B). Younger bark on limbs grey (RHS 201A).

*Density*.—Light to medium in branching habit.

*Hardiness*.—Hardy with respect to central Georgia winters.

*Productivity*.—Very rarely produces fruit. In some years a mature tree may produce several fruit; in other years there is no fruit.

*Chilling requirement*.—Estimated endodormancy chilling requirement is approximately 850 chill units based on time of bloom and leafing in relation to standard varieties.

Branches:

*Size*.—Strong growth of scaffold branches; diameter of scaffold limbs at the trunk is approximately 7 cm.

*Texture*.—Relatively smooth, medium size lenticels attaining size found on trunk and old scaffolds; roughness increases with age.

*Color*.—New wood is yellow-green (RHS 145A); some twigs may be speckled or streaked greyed-purple (RHS 184B) on the side facing the sun. Previous year twigs were a mix of greyed-orange (RHS 165A) and greyed-green (RHS 191B).

*Crotch angles*.—Angles are approximately 60 degrees from vertical or the main branch axis, within normal range of standard varieties for a semi-spreading tree.

Foliage:

*Form*.—Lanceolate.

*Apex*.—Acute.

*Base*.—Cuneate.

*Margin*.—Serrulate, slightly undulate.

*Size*.—Medium. Average length including the petiole: 170 mm. Average width: 39 mm.

*Thickness*.—Regular and average for commercial peach varieties.

*Surface of blade*.—Upper, glabrous, color yellow-green RHS 147A; Lower, medium large veins that are pinnately netted, color yellow-green (RHS 147B). New growth of leaves may have dark greyed-purple portions RHS 187A on the top and RHS 187B underneath. Some leaves may also have a greyed-purple main vein RHS 184B visible on the underside.

*Glands*.—Usually about 2-4, medium size reniform glands on lower leaf blade, and petiole; leaf glands on young leaves are yellow-green RHS 146C.

*Petiole*.—Length about 9 mm; diameter 1.5 mm; color yellow-green (RHS 146C); shape is grooved longitudinally.

*Stipules*.—Medium, equal to most commercial peach varieties; usually 2 per leaf, and abscising just before leaf becomes full size in summer growth; color at full size is yellow-green RHS 145A, but tinged with anthocyanin before abscising.

*Arrangement*.—Alternate.

Flower buds:

*Hardiness*.—Hardy with respect to central Georgia winters.

*Abundance*.—Medium-high.

*Size*.—Medium, average approximately 5 mm in length. Flower buds may reach approximately 1.5 cm just prior to opening fully.

*Form*.—Plump, conic, and free.

*Surface*.—Pubescent scales.

Flowers:

*Date of bloom*.—Blooming in Byron, Ga. usually starts in mid March and lasts about 2 weeks, depending on ambient temperatures.

*Aroma*.—None.

*Flower density*.—Abundant, varying from about 1 to 3 per node, but usually 2.

*Type*.—Double showy; flower diameter very large, approximately 6.7 cm; approximately 35-40 petals.

*Texture*.—Smooth.

*Margins*.—Undulate and smooth.

*Petals*.—Color may be white (whiter than RHS 155C), pink (red RHS 55C or 56C), red (RHS 54A), or a mixture of these colors. Shape oval. Length approximately 20-25 mm; width mostly 15-20 mm, but some central petals only 10 mm.

*Sepals*.—Approximately 8-10 mm in length and approximately 5 mm wide at attachment to calyx cup and rounded at the distal end; green (RHS 134C), sometimes with greyed-purple sectors (RHS 183A); pubescent; approximately 8-12 in number.

*Pistils*.—Usually 1 per flower and straight (without curls or curves) just prior to flower opening; length from tip of stigma to base of ovary is approximately 15-25 mm.

*Flower pedicel*.—Approximately 6-10 mm in length.

*Calyx cup*.—Large.

*Stamen*.—Anthers are yellow (RHS 9B) at pollen shed; filament length is approximately 20 mm; number is approximately 45-55. Some may be petalloid, with petal tissue of about 5 mm width terminating a stamenoid stalk.

*Pollen*.—Yellow (RHS 9B), limited in quantity, germinates poorly.

*Fertility*.—Mostly infertile even with cross-pollination.

Fruit:

*Maturity*.—Tree ripe, mid August at Byron, Ga.

*Size*.—Small, approximately 5 cm in diameter.

*Penduncle*.—Length longer than most peaches at approximately 6-10 mm; width is approximately 1-2 mm.

*Suture*.—Shallow and inconspicuous except for a crease at the stem end.

*Skin*.—Medium thickness in comparison to commercial peach varieties; color when immature is yellow-green RHS 145B; mature fruit is mostly lighter yellow-green RHS 145C with some areas yellow-green RHS 150C.

*Texture*.—Medium in comparison to standard varieties.

*Tenacity*.—Tenacious to flesh.

*Taste*.—Fair flavor, but inferior to commercial peaches.

*Epidermis*.—Pubescent.

*Texture*.—Firm but juicy and non-melting when fully ripe.

*Aroma*.—Moderate and in the middle range of commercial peach varieties.

*Flesh color*.—Generally "white" but retains some greenish tint even when ripe (yellow-green RHS 145D), with no red in the flesh or at the pit.

Stone:

*Type*.—Clingstone; medium small size; length approximately 23 mm, width approximately 20 mm, thickness approximately 15 mm.

*Color*.—Greyed-orange (RHS 165C) when flesh is freshly cut.

*Form*.—Slightly oblong.

*Base*.—Pointed.

*Apex*.—Rounded.

*Sides*.—Near equal.

*Surface*.—Irregularly shallow furrowed and pitted.

*Ridges*.—Shallow and rounded.

Resistance to insects, disease, or pests:

*Bacteria*.—Moderate resistance to bacterial spot incited by *Xanthomonas campestris* pv. *pruni* (Pers.) Diet.

*Resistance to other fruit and tree diseases*.—Within the range for commercial peach cultivars; no unusual resistance or susceptibility to insects and diseases noted.

I claim:

1. A new and distinct variety of ornamental peach tree 'Candy Cane', substantially as illustrated and described, having large, tri-colored flowers and bi-colored variegated leaves and bi-colored variegated leaves and shoots.

* * * * *